United States Patent [19]

Bilstad et al.

[11] 4,294,320

[45] Oct. 13, 1981

[54] METHOD AND APPARATUS FOR WEIGHING MATERIAL BEING COLLECTED

[75] Inventors: Arnold C. Bilstad, Deerfield; John T. Foley, Wheeling, both of Ill.

[73] Assignee: Baxter Travenol Laboratories, Inc., Deerfield, Ill.

[21] Appl. No.: 127,734

[22] Filed: Mar. 6, 1980

[51] Int. Cl.³ .................... G01G 13/00; G01G 23/14
[52] U.S. Cl. ........................................ 177/1; 177/165; 177/DIG. 3; 235/92 WT
[58] Field of Search ........... 177/165, 210 FP, DIG. 3, 177/1, 25, 164; 235/92 WT

[56] References Cited

U.S. PATENT DOCUMENTS

| | | | |
|---|---|---|---|
| 3,684,875 | 8/1972 | Smith | 235/92 WT X |
| 3,853,267 | 12/1974 | Cadwell | 235/92 WT X |
| 3,924,700 | 12/1975 | Lindsay | 177/118 |
| 4,044,846 | 8/1977 | Matilainen | 177/165 |

Primary Examiner—Joseph W. Hartary
Attorney, Agent, or Firm—Paul Flattery; George Gerstman

[57] ABSTRACT

Process and apparatus for weighing material being collected. In the illustrative embodiment, plasma that has been separated from whole blood is collected. The tare weight is sensed and the weight of the material being collected is sensed. Pulses are provided in frequency proportion to the sensed weight. The tare weight pulses are counted and stored. A net weight counter is set with a predetermined count corresponding to the maximum amount of plasma to be collected. A measure weight signal reverses the tare weight count with the net weight counter being inhibited until the tare weight count reversal has been completed. Once the tare weight count reversal is completed, the net weight counter is operative to count the sensed weight pulses. A completion signal is provided when the predetermined count has been decremented to zero.

23 Claims, 1 Drawing Figure

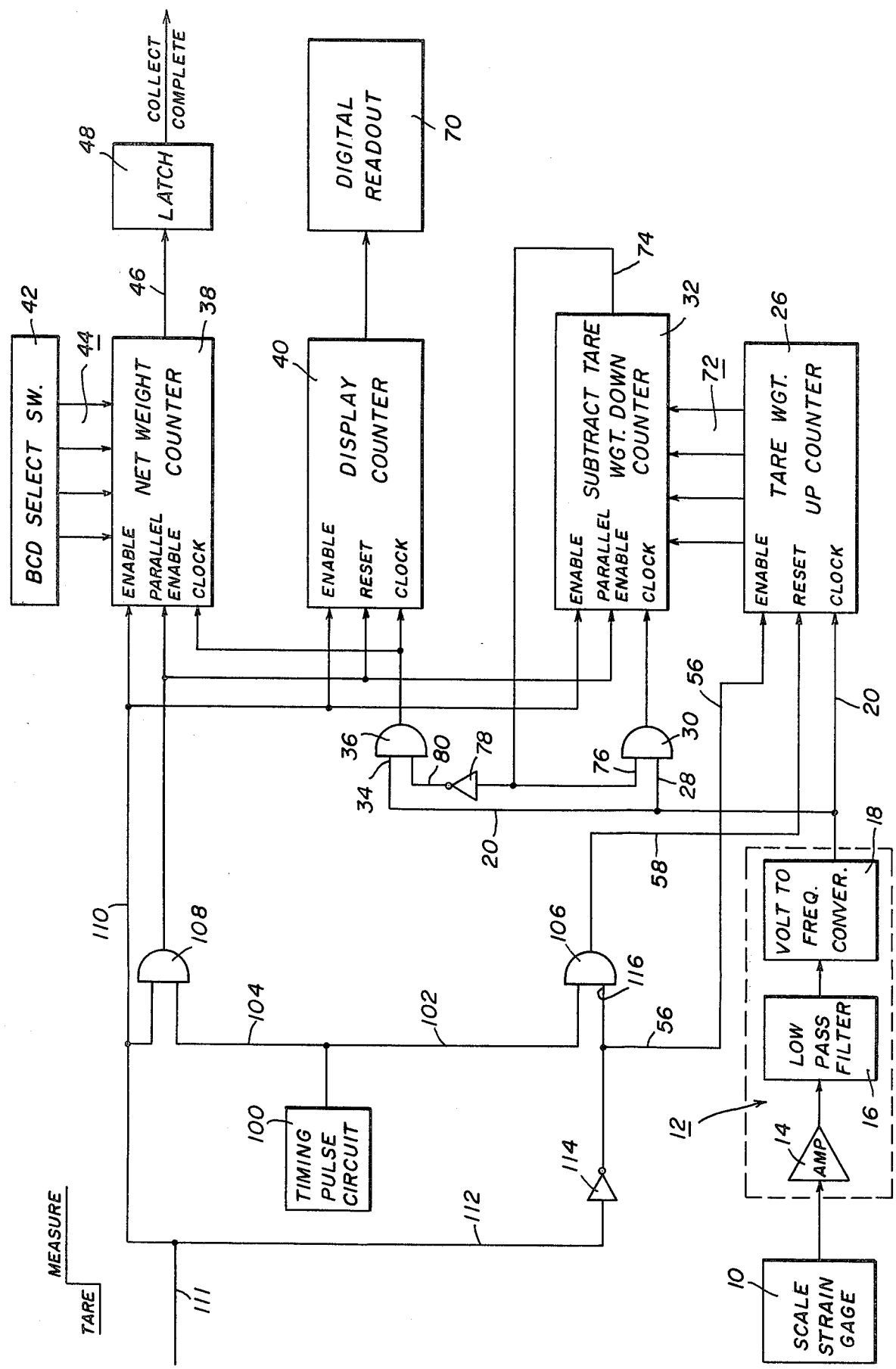

METHOD AND APPARATUS FOR WEIGHING MATERIAL BEING COLLECTED

BACKGROUND OF THE INVENTION

The present invention concerns a novel apparatus for weighing material being collected. Although the illustrative embodiment describes a system in which plasma that is separated from whole blood is being collected, it is to be understood that the apparatus and method of the present invention is applicable to weighing various materials being collected. Further, since weight is proportional to volume the apparatus and method of the present invention is applicable to determining the volume of material being collected. As used herein, the term "weight" should be considered as interchangeable with "volume".

Plasmapheresis involves the separation of plasma from whole blood, the collection of the plasma and the return of the red cells to the donor. It is desirable, if not essential, that the weight (i.e., volume) of the plasma being collected be monitored. In some cases, the plasma is collected in a disposable plastic container which may be hung from a suitable post or rack.

Monitoring the amount of plasma collected from a patient or donor is essential because the collection of too much plasma may be dangerous and it is desirable to effect a predetermined yield. Thus a doctor may weigh the patient or donor and determine from such weight how much plasma can safely be collected.

It is an object of the present invention to provide an apparatus and method for weighing material (such as plasma) being collected, with the provision of signaling or terminating the operation when a predetermined amount of the material has been collected.

Another object of the present invention is to provide an apparatus for weighing material being collected, which apparatus is relatively simple in construction and easy to manufacture.

A further object of the present invention is to provide apparatus for weighing material being collected, which apparatus is relatively accurate and employs digital circuitry.

Another object of the present invention is to provide apparatus for weighing material being collected, which apparatus is relatively insensitive to lead length and contact resistance.

A further object of the present invention is to provide apparatus for weighing material being collected, which apparatus operates automatically to compensate for the tare weight.

A still further object of the present invention is to provide an automatic system for weighing material being collected, which utilizes digital components and provides a result display.

Another object of the present invention is to provide apparatus and a method for weighing material being collected, which is simple to operate and is adaptable for measuring the weight or volume of plasma being collected during plasmapheresis.

Other objects and advantages of the invention will become apparent as the description proceeds.

SUMMARY OF THE INVENTION

In accordance with the present invention, a system is provided for weighing material being collected. The tare weight of the weight and collection apparatus is sensed and the weight of the material being collected is sensed. Pulses are provided in frequency proportional to the weight that is sensed. The tare weight pulses are counted and stored. A net weight counter is set with a predetermined count corresponding to the maximum weight to be collected. A measure weight signal is provided to reverse the tare weight count. The net weight counter is inhibited until the tare weight count reversal has been completed. Thereafter, the net weight counter is operated to count the sensed weight pulses. A completion signal is provided when the predetermined count has been removed from the net weight counter.

In the illustrative embodiment, a display counter is provided for counting the pulses with the net weight counter and a digital readout is provided for displaying the net weight collected.

In the illustrative embodiment, a tare weight upcounter is provided for counting the tare weight pulses and for storing the tare weight count. A subtract tare weight downcounter is loaded with the tare weight count and is decremented in response to the measure weight signal.

In the illustrative embodiment, the counting operation is recycled at predetermined time periods, with the recycling means comprising a real time clock which provides clock pulses to update the weight collection measurement each predetermined time period.

In the illustrative embodiment, the net weight counter is set by the doctor or nurse with a BCD switch, and this setting will correspond to the maximum amount of material, such as plasma, to be collected. Once this maximum has been collected, the operation of the collection apparatus may be terminated.

A more detailed explanation of the invention is provided in the following description and claims, and is illustrated in the accompanying drawing.

BRIEF DESCRIPTION OF THE DRAWING

The drawing comprises a schematic circuit diagram of an apparatus for weighing material being collected, constructed in accordance with the principles of the present invention.

DETAILED DESCRIPTION OF THE ILLUSTRATIVE EMBODIMENT

Referring to the drawing, a conventional strain gauge 10, which is preferably a resistance bridge circuit, is responsive to the weight of the plasma to be determined. The output of plasma strain gauge 10 is fed to a preamplifier circuit 12 which includes an amplifier 14 having a zero calibration input and a gain calibration input. The output of amplifier 14 is coupled to a low pass filter 16 so as to remove the high frequency components. The output of low pass filter 16 is coupled to a voltage to frequency converter 18. The conversion may be such that converter 18 operates to provide a frequency of 1 hertz per gram or 1 hertz per milliliter. This is the clock signal that will be fed to counters to be described.

The clock signal is fed via line 20 to a clock input of tare weight up-counter 26. Clock line 20 is also fed to the inlet 28 of an AND gate 30, the output of which is fed to the clock input of subtract tare weight downcounter 32. Clock line 20 is also fed to an input 34 of AND gate 36, the output of which is fed to the clock input of net weight down-counter 38 and the clock input of display up-counter 40.

A BCD select switch 42 is coupled to the jam input of net weight down-counter 38 via lines 44. The output of counter 38 is fed via line 46 to a latch 48 in the form of a flip-flop, the output of which is a "collection complete" control signal, designating that the desired amount of fluid has been collected.

The output of display counter 40 is a multiplexed signal that is fed to a conventional digital readout device 70.

Tare weight up-counter 26 is coupled to subtract tare weight down-counter 32 by lines 72 which provide a digital signal to load the down-counter 32 with the count from counter 26. An output 74 of counter 32 is fed to input 76 of AND gate 30 and to an inverter 78, the output of which inverter 78 is fed via line 80 to an input 82 of AND gate 36. As previously described, the output of AND gate 36 is fed to the clock inputs of display up-counter 40 and net weight down-counter 38.

A timing pulse circuit 100 is provided for providing real time clock pulses along line 102 and line 104. Line 102 feeds to an input of AND gate 106, the output of which is connected to the reset input of counter 26. Line 104 is fed to an input of AND gate 108, the output of which is connected to the parallel enable input of counter 38, the reset input of counter 40 and the parallel enable input of counter 32. An enable signal is provided via line 110 to the enable inputs of counters 38, 40 and 32.

An enable signal is provided on line 110 only when a logic signal on line 111 is in the "measure" mode. When line 111 is carrying a "tare" mode logic signal, the signal is provided via line 112 to inverter 114 and from inverter 114 to input 116 of AND gate 106 and also from inverter 114 via line 56 to the enable input of counter 26. The logic signal on line 111 may be a low to represent the measure mode.

In the operation of the system, when the logic signal is low to represent the tare mode, line 110 is low so counters 38, 40 and 32 are not enabled. On the other hand, line 112 is low so that when inverted by inverter 114, input 116 becomes high and a timing pulse via line 102 is fed to the reset input of counter 26. Counter 26 is reset and the clock pulses via line 20 count counter 26 up to the tare weight. In the tare mode, counter 26 is the only counter that is enabled, via line 56. The timing cycle is such that counter 26 is forced to count up one complete time so that even if the system is switched to the measure mode, the counter 26 will count up the entire tare weight.

When the system is switched to the measure mode, a high signal is provided via line 110 to enable counters 38, 40 and 32. When line 110 is high, a timing pulse from line 104 through AND gate 108 parallel enables counters 38 and 32 and resets counter 40. Counter 32, when parallel enabled, loads with the tare weight from counter 26 via line 72. Counter 38, when parallel enabled, loads with the count from BCD select switch 42 via lines 44. Now counters 32 and 38 are loaded with the tare weight and selected weight, respectively. As long as there is a parallel enable signal to counters 32 and 38, these counters will not count but will only hold the value that is being loaded into them. Once counters 32 and 38 are parallel enabled and loaded with the tare weight and selected weight, respectively, the clock pulses via line 20 (carrying a frequency correlated to the weight) will clock counter 32 down. Once counter 32 is clocked down to zero (the entire tare weight is unloaded), a pulse will be fed via output 74 to inverter 78 which will enable AND gate 36 thus enabling the clock input of display counter 40 and the clock input of down-counter 38. Thus counter 40 will begin counting up while counter 38 counts down. At the same time, the zero signal from output 74 of counter 32 will be fed back to input 76 of AND gate 30 and effectively shut counter 32 off.

Counter 38 will count down until its output is zero. If the rate of 500 units (e.g., grams or ml.) has been selected by select switch 42 and loaded into counter 38, once the 500 units are counted down and a zero signal is on line 46, the latch 48 will operate to provide a "collection complete" control signal. At the same time, display counter 40 has counted up the 500 units and the digital readout 70 will display what is in counter 40.

Every second the system goes through a cycle and in effect continually samples the output on line 20. It will continue to sample the output on line 20 until counter 38 has counted down to zero.

It can be seen that by using frequency pulses that are proportional to the weight instead of using an analog voltage that is proportional to the weight, the amount of voltage can vary somewhat so that the lead length and the contact resistance can be somewhat variable without affecting the system. In this manner, accuracy is not lost so long as pulses are provided in a frequency proportional to the weight. If the amplitude of the voltage with respect to providing such frequency pulses is lost, there will be no pulse output and the system will readily show that there is a problem instead of providing an incorrect reading as might occur if an analog voltage system were used. The apparatus can be simply calibrated by attaching a known weight and determining if the frequency is correct.

Although an illustrative embodiment of the invention has been shown and described, it is to be understood that various modifications and substitutions may be made without departing from the novel spirit and scope of the invention.

What is claimed is:

1. A process for weighing material being collected, which comprises the steps of:
    sensing the tare weight of the weight and collection apparatus;
    sensing the weight of the material being collected;
    providing pulses in frequency proportion to the weight sensed;
    counting the tare weight pulses;
    storing the tare weight count;
    setting a net weight counter with a predetermined count corresponding to the maximum weight to be collected;
    providing a measure weight signal to reverse the tare weight count;
    inhibiting the net weight counter until the tare weight count reversal has been completed;
    thereafter operating the net weight counter to count the sensed weight pulses; and
    providing a completion signal when the predetermined count has been removed from the net weight counter.

2. A process for weighing material being collected as described in claim 1, including the steps of providing a display counter for counting the pulses with the net weight counter and providing a digital readout for displaying the net weight collected.

3. A process for weighing material being collected as described in claim 1, including the steps of providing a tare weight up-counter for counting the tare weight pulses and providing a subtract tare weight down-counter for receiving the tare weight count.

4. A process for weighing material being collected as described in claim 3, including the step of decrementing the subtract tare weight down-counter in response to the measure weight signal.

5. A process for weighing material being collected as described in claim 1, including the step of recycling the counting operation at predetermined time periods.

6. A process for weighing material being collected as described in claim 5, said recycling step comprising providing real time clock pulses to update the weight collection measurement each predetermined time period.

7. A process for weighing material being collected, which comprises the steps of:
   sensing the tare weight of the weight and collection apparatus;
   sensing the weight of the material being collected;
   providing pulses in frequency proportion to the weight sensed;
   providing a tare weight up-counter for counting the tare weight pulses;
   providing a subtract tare weight down-counter for receiving the tare weight count;
   setting a net weight counter with a predetermined count corresponding to the maximum weight to be collected;
   providing a measure weight signal to reverse the tare weight count by decrementing the subtract tare weight down counter in response to the measure weight signal;
   inhibiting the net weight counter until the tare weight count reversal has been completed;
   thereafter operating the net weight counter to count the sensed weight pulses;
   providing a completion signal when the predetermined count has been removed from the net weight counter;
   providing a display counter for counting the pulses with the net weight counter;
   providing a digital readout for displaying the net weight collected; and
   recycling the counting operation at predetermined time periods.

8. Apparatus for weighing material being collected, which comprises:
   means for sensing the weight of the material being collected;
   means for providing pulses in frequency proportion to the weight sensed by said sensing means;
   tare weight counting means having a count input and an enable input;
   means coupled to said enable input for enabling said tare weight counting means in response to a tare weight signal;
   means coupling said pulse providing means to said count input;
   a net weight counter having a clock input and an enable input;
   a switch connected to said net weight counter for setting said counter with a predetermined count;
   means coupled to the enable input of said net weight counter for enabling said net weight counter in response to a measure weight signal;
   means coupling said pulse providing means to the count input of said net weight counter;
   means for reversing the count direction of said tare weight counter means in reponse to a measure weight signal;
   means for inhibiting said net weight counter from being enabled until said tare weight counting means has first completed its count reversal;
   means for providing an output signal from said tare weight counting means to said net weight counter when said tare weight counting means has completed its count reversal;
   said net weight counter being responsive to said signal from said tare weight counting means to count the pulses presented to the clock input of said net weight counter, said count being in a direction opposite to said predetermined count set with said switch; and
   means coupled to said net weight counter for providing a completion signal in response to removal of said predetermined count.

9. Apparatus for weighing material being collected as described by claim 1, including a display counter coupled to said net weight counter and operable to count with said net weight counter; and
   digital readout means coupled to said display counter for displaying the net weight collected.

10. Apparatus for weighing material being collected as described in claim 9, said display counter comprising an up-counter operative to provide multiplexed readout signals corresponding to the counts.

11. Apparatus for weighing material being collected as described in claim 1, said sensing means comprising a strain gauge.

12. Apparatus for weighing material being collected as described in claim 11, said pulse providing means comprising a voltage to frequency converter.

13. Apparatus for weighing material being collected as described in claim 1, said tare weight counting means comprising a tare weight up-counter and a subtract tare weight down-counter coupled thereto.

14. Apparatus for weighing material being collected as described in claim 13 including means coupled to said subtract tare weight down-counter for enabling said subtract tare weight down counter in response to a measure weight signal;
   said output signal means being operative to provide an output signal from said subtract tare weight down-counter when it has decremented to zero.

15. Apparatus for weighing material being collected as described in claim 1, said net weight counter comprising a down-counter operative to count down in response to receipt of pulses at its clock input.

16. Apparatus for weighing material being collected as described in claim 15, said net weight counter having a jam input and said switch comprising a BCD switch coupled to said jam input.

17. Apparatus for weighing material being collected as described in claim 1, said completion signal providing means comprising a latch coupled to the output of said net weight counter.

18. Apparatus for weighing material being collected as described in claim 1, including timing means for recycling the counting operation at predetermined time periods.

19. Apparatus for weighing material being collected as described in claim 18, said timing means comprising means for providing real time clock pulses to the counters whereby the weight collection measurement is updated each predetermined time period.

20. Apparatus for weighing material being collected, which comprises:

a strain gauge for sensing the weight of the material being collected;

a voltage to frequency converter for providing pulses in frequency proportion to the weight sensed by said strain gauge;

a tare weight up-counter having a count input and an enable input;

a subtract tare weight down-counter coupled to said tare weight up-counter;

means coupled to said enable input for enabling said tare weight up-counter in response to a tare weight signal;

means coupling said voltage to frequency converter to said count input;

a net weight counter having a clock input and an enable input;

a switch connected to said net weight counter for setting said counter with a predetermined maximum count;

means coupled to the enable input of said net weight counter for enabling said net weight counter in response to a measure weight signal;

means coupling said voltage to frequency converter to the count input of said net weight counter;

means for transferring the tare weight from said tare weight up-counter to said subtract tare weight downcounter;

means for decrementing said subtract tare weight down-counter in response to a measure weight signal;

means for inhibiting said net weight counter from being enabled until said subtract tare weight down-counter has decremented to zero;

means for providing an output signal from said subtract tare weight down-counter to said net weight counter when said subtract tare weight down-counter has decremented to zero;

said net weight counter being responsive to said output signal to count the pulses presented to the clock input of said net weight counter, said count being in a direction opposite to said predetermined count set with said switch; and means coupled to said net weight counter for providing a completion signal in response to removal of said predetermined maximum count.

21. Apparatus for weighing material being collected as described in claim 20, said net weight counter comprising a down-counter operative to count down in response to receipt of pulses at its input, said net weight counter having a jam input, said switch comprising a BCD switch coupled to said jam input.

22. Apparatus for weighing material being collected as described in claim 20, including a display counter coupled to said net weight counter and operable to count with said net weight counter; and digital readout means coupled to said display counter for displaying the net weight collected.

23. Apparatus for weighing material being collected as described in claim 20, including timing means recycling the counting operation at predetermined time periods, said timing means comprising means for providing real time clock pulses to the counters whereby the weight collection measurement is updated each predetermined time period.

* * * * *